United States Patent [19]

Portlock

[11] Patent Number: 4,461,896
[45] Date of Patent: Jul. 24, 1984

[54] 1-[ACYLTHIO) AND (MERCAPTO)-1-OXOALKYL]-1,2,3,4-TETRAHYDROQUINOLINE-2-CARBOXYLIC ACIDS

[75] Inventor: David E. Portlock, Norwich, N.Y.

[73] Assignee: Norwich Eaton Pharmaceuticals, Inc., Norwich, N.Y.

[21] Appl. No.: 90,862

[22] Filed: Nov. 2, 1979

Related U.S. Application Data

[63] Continuation-in-part of Ser. No. 10,165, Feb. 7, 1979, abandoned.

[51] Int. Cl.³ .................... A61K 31/47; C07D 215/48
[52] U.S. Cl. ...................................... 546/165; 424/274
[58] Field of Search ........................................... 546/165

[56] References Cited

U.S. PATENT DOCUMENTS 4,104,392  9/1978  Okamoto et al. .................. 546/165

Primary Examiner—Paul M. Coughlan, Jr.
Assistant Examiner—D. B. Springer

[57] ABSTRACT

A series of 1-[acylthio) and (mercapto)-1-oxoalkyl]-1,2,3,4-tetrahydroquinoline-2-carboxylic acids and salts thereof are useful as Angiotensin I converting enzyme inhibitors.

39 Claims, No Drawings

1-[(ACYLTHIO) AND (MERCAPTO)-1-OXOALKYL]-1,2,3,4-TETRAHYDROQUINOLINE-2-CARBOXYLIC ACIDS

This application is a continuation-in-part of our copending application Ser. No. 010,165 filed Feb. 7, 1979, abandoned.

This invention is concerned with compounds of the formula:

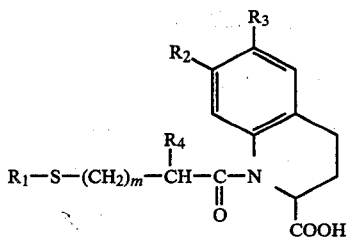

wherein $R_1$ is benzoyl, acetyl, hydrogen or

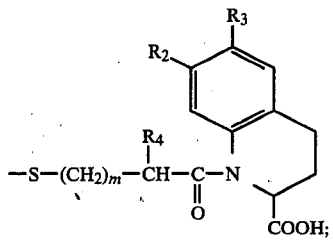

$R_2$ is hydrogen, methoxy or methyl; $R_3$ is hydrogen, methoxy, methyl, chloro or hydroxy; $R_4$ is hydrogen, methyl or acetylthiomethyl; m is 0 or 1 and the sodium and dicyclohexylamine salts thereof. Manifestly the compounds represented by formula (I) exist in diastereoisomeric forms or in racemic mixtures thereof; all being within the scope of this invention. Generally, the stereoisomeric form having the S(L) absolute configuration is preferred.

These compounds are potent inhibitors of the enzyme responsible for converting the decapeptide Angiotensin I to the octapeptide Angiotensin II. Angiotensin II is the powerful pressor agent implicated as the caustive agent in some forms of hypertension.

Of late, it has been recognized that a substance capable of interrupting the pathway whereby Angiotensin II is produced, viz.; the conversion hereabove referred to, presents a useful and effective means of combatting hypertension associated with that pressor agent.

It has been discovered that the compounds of this invention are possessed of noteworthy activity in inhibiting Angiotensin I converting enzyme. Thus, in in vitro techniques designed to evince such activity these compounds are highly effective. For example, they inhibit the pure converting enzyme isolated from rabbit lung tissue at levels from about 0.039 μm to 8.80 μm. They are, therefore, notable Angiotensin I converting enzyme inhibitors.

The compounds of this invention are not limited to in vitro manifestations of their converting enzyme inhibiting propensity. Upon oral administration, a dose-dependent antihypertensive effect in acute aortic coarctation hypertensive rats is elicited. Oral dosages of from 0.33 mg/kg to 200 mg/kg administered as a suspension in 0.5% Methocel solution achieve a reduction of 30 mm. Hg. in mean arterial blood pressure in such rats.

The compounds of this invention can be composed in a variety of dosage forms such as tablets, capsules, solutions and the like for convenient administration employing classical excipients and adjuvants with which there is no incompatibility. Such dosage forms contain from 10 to 500 mg of a compound of formula (I) or a salt thereof in a unit dosage form in accordance with accepted pharmaceutical practice.

In order that this invention may be readily available to and understood by those skilled in the art, the following examples describe currently preferred methods for the preparation of the compounds thereof.

EXAMPLE 1

(±)-1,2,3,4-Tetrahydro-2-quinolinecarboxylic Acid Hydrochloride

2-Quinolinecarboxylic acid (30 g), glacial acetic acid (500 ml), and $PtO_2$ (0.9 g) were combined and hydrogenated at 50°–58° for 45 minutes. After cooling to room temperature, concentrated hydrochloric acid (35 ml) was added, the catalyst was filtered, and the filtrate evaporated in vacuo. The residue was dissolved in acetonitrile (200 ml) and the solution cooled overnight. The resulting product was filtered; yield 25 g, m.p. 122°–125°.

EXAMPLE 2

(S)(−)-1,2,3,4-Tetrahydro-2-quinolinecarboxylic Acid Hydrochloride (±)-1,2,3,4-Tetrahydro-2-quinolinecarboxylic acid hydrochloride (113 g), water (500 ml), and 2 N sodium hydroxide (500 ml) were combined and the resulting stirred solution was cooled with an ice bath. This solution was kept at 0°–5° while benzyl chloroformate (85 ml) and 1 N sodium hydroxide (500 ml) were added slowly over a two hour period. After stirring another four hours at 0°–10°, the basic solution was extracted with ethyl acetate. The aqueous layer was then acidified to pH 2 with concentrated hydrochloric acid and extracted with ethyl acetate. The ethyl acetate extracts from the acidified aqueous layer were combined and washed with 1 N hydrochloric acid, dried over magnesium sulfate with activated charcoal and concentrated to dryness in vacuo. The residue was recrystallized from ethyl acetate-hexanes; yield 97 g, m.p. 103°–105°.

The (±)-1,2,3,4-tetrahydro-1-phenylmethoxycarbonyl-2-quinolinecarboxylic acid thus obtained was further characterized as its dicyclohexylamine salt which was often useful for the isolation, recovery and/or purification of the parent acid. (±)-1,2,3,4-Tetrahydro-1-phenylmethoxycarbonyl-2-quinolinecarboxylic acid (59 g) was dissolved in ether and dicyclohexylamine was added until the solution was basic to wet litmus paper. The resulting salt was collected by filtration and recrystallized from methanol; yield 72 g, m.p. 196°–197°.

(±)-1,2,3,4-Tetrahydro-1-phenylmethoxycarbonyl-2-quinolinecarboxylic acid (243 g) was dissolved with warming in 2-propanol (1170 ml) and this solution was treated with (S)(−)-α-methylbenzylamine (100 ml). After stirring overnight, the solid product was filtered and dried to constant weight at 60°; yield 160 g, m.p. 135°–148°, $[\alpha]_D^{20}$ −25.6° (c 1, methanol). This crystalline salt was recrystallized from 2-propanol (1400 ml) and washed with ether (400 ml); yield 108 g, m.p. 155°–159°, $[\alpha]_D^{20}$ −50.0° (c 1, methanol). This product was again recrystallized from 2-propanol (1100 ml) and washed with ether (500 ml); yield 84 g, m.p. 159°–160°, $[\alpha]_D^{20} -54.9°$ (c 1, methanol). This salt was added to a mixture of ethyl acetate (500 ml) and 5% aqueous potassium hydrogen sulfate (1000 ml) and stirred for one hour. The layers were separated and the aqueous layer extracted with additional ethyl acetate (250 ml). The organic phase and extract were combined and washed with water (500 ml), dried over magnesium sulfate and activated charcoal, and concentrated to an oily residue which rapidly crystallized to yield (S)(−)-1,2,3,4-tetrahydro-1-phenylmethoxycarbonyl-2-quinolinecarboxylic acid, 57 g, m.p. 75°–79°, $[\alpha]_D^{20} -82.9°$ (c 1, methanol). This product was dissolved in methanol (400 ml) and hydrogenated over 5% Pd on carbon (2.0 g) at 40 psi for three hours. The catalyst was filtered and the filtrate concentrated under reduced pressure to an oily residue. Addition of concentrated hydrochloric acid (30 ml) to the residue gave (S)(−)-1,2,3,4-tetrahydro-2-quinolinecarboxylic acid hydrochloride; yield 23.6 g, m.p. 172°–176°, $[\alpha]_D^{20} -17°$ (c 1, 0.5 N HCl).

EXAMPLE 3

(R)(+)-1,2,3,4-Tetrahydro-2-quinolinecarboxylic Acid Hydrochloride

The 2-propanol filtrates obtained in Example 2 were combined and concentrated to yield a mixture of salts enriched in the (R)(+)-1,2,3,4-tetrahydro-1-phenylmethoxycarbonyl-2-quinolinecarboxylic acid (S)α-methylbenzylamine salt diastereomer. This material was recrystallized from 2-propanol, m.p. 129°–130°, $[\alpha]_D^{20} +53.3°$ (c, 1, methanol). This salt (39 g) was added to a mixture of ethyl acetate (200 ml) and 10% aqueous potassium hydrogen sulfate (200 ml) and stirred for one hour. The layers were separated and the aqueous layer extracted with ethyl acetate (100 ml). The organic phase and extracted were combined and washed with water (200 ml), dried over magnesium sulfate, and concentrated to an oil which rapidly crystallized; yield 23 g, m.p. 80°–82°, $[\alpha]_D^{20} +83.1°$ (c 1, methanol).

This product was dissolved in methanol (300 ml) and hydrogenated over 5% Pd on carbon (1 g) at 40 psi for one hour. The catalyst was filtered and the filtrate concentrated under reduced pressure to an oily residue. Addition of concentrated hydrochloric acid (20 ml) to the residue gave (R)(+)-1,2,3,4-tetrahydro-2-quinolinecarboxylic acid hydrochloride; yield 22.5 g, m.p. 177°–182°, $[\alpha]_D^{20} +16.9°$ (c 1, 0.5 N HCl).

EXAMPLE 4

(±)-1-(3-Benzoylthio-1-oxopropyl)-1,2,3,4-tetrahydro-2-quinolinecarboxylic Acid (±)-1,2,3,4-Tetrahydro-2-quinolinecarboxylic acid hydrochloride (38.1 g) was dissolved in a cold (0°) solution of sodium hydroxide (14.3 g) and water (350 ml). 3-Bromopropionyl chloride (30.6 g) and a solution of sodium hydroxide (7.2 g) in water (90 ml) were added dropwise with rapid stirring and this mixture was stirred at room temperature for 3.5 hours. A solution of potassium thiobenzoate (30.8 g) in water (168 ml) was then added and the mixture was stirred for 20 hours at room temperature. The reaction solution was then cooled in an ice bath for 1.5 hours and the resulting crystalline solid collected by filtration. It was washed three times with cold water, cold 2-propanol, and ether and finally recrystallized from ethanol; yield 70 g, m.p. 193°–195°.

The (±)-1-(3-benzoylthio-1-oxopropyl)-1,2,3,4-tetrahydro-2-quinolinecarboxylic acid sodium salt thus obtained (70 g) was stirred in cold water (300 ml) and acidified with 20% hydrochloric acid (35 ml) while cooling in an ice bath. This resulting mixture was extracted several times with ether (1300 ml) and the extract dried over sodium sulfate and concentrated under reduced pressure to yield a solid residue. This product (43 g) was dissolved in acetonitrile (200 ml) and dicyclohexylamine (22 g) was added while cooling in an ice bath. The crystalline product was collected by filtration and washed four times with cold acetonitrile (20 ml); yield 51 g. The product was recrystallized from ethanol, m.p. 165°–167°.

The (±)-1-(3-benzoylthio-1-oxopropyl)-1,2,3,4-tetrahydro-2-quinolinecarboxylic acid dicyclohexylamine salt thus obtained (35.6 g) was suspended in 2-propanol (200 ml) and this mixture was treated with a solution of dry hydrogen chloride in 2-propanol (27 ml) with cooling in an ice bath. The resulting dicyclohexylamine hydrochloride was filtered and washed twice with 2-propanol (20 ml). The combined filtrate and washings were concentrated under reduced pressure. The residue was dissolved in ether (300 ml) and this solution was dried over sodium sulfate and concentrated under reduced pressure to give 23.6 g of (±)-1-(3-benzoylthio-1-oxopropyl)-1,2,3,4-tetrahydro-2-quinolinecarboxylic acid, m.p. 99°–101°.

EXAMPLE 5

(S)(−)-1-(3-Benzoylthio-1-oxopropyl)-1,2,3,4-tetrahydro-2-quinolinecarboxylic Acid 3-Benzoylthiopropanoic acid (6.4 g) in toluene was treated with thionyl chloride (2.6 ml). The resulting solution was warmed to 60° for two hours and then evaporated to dryness under reduced pressure to yield 3-benzoylthiopropanoyl chloride. A solution of (S)(−)-1,2,3,4-tetrahydro-2-quinolinecarboxylic acid hydrochloride (6.5 g) in pyridine (45 ml) was treated dropwise with the crude 3-benzoylthiopropanoyl chloride with vigorous stirring. After stirring overnight, pyridine hydrochloride was filtered and the filtrate was added to a mixture of ice (500 g) and ether (100 ml). The mixture was acidified with concentrated hydrochloric acid and then extracted with ether. The ether layer was dried with sodium sulfate, activated charcoal, and silica gel and then concentrated to dryness to yield a viscous oil (11.2 g). This residue was dissolved in acetonitrile (40 ml) and dicyclohexylamine (7 ml) was added. The crystalline product was collected by filtration, washed with cold acetonitrile, and ether, and recrystallized from ethanol (70 ml), yield 6 g, m.p. 158°–160°, $[\alpha]_D^{20} -158.2°$ (c 1, methanol).

The (S)(−)-1-(3-benzoylthio-1-oxopropyl)-1,2,3,4-tetrahydro-2-quinolinecarboxylic acid dicyclohexylamine salt thus obtained (5.5 g) was suspended in 2-propanol (30 ml) and this mixture was treated with a solution of dry hydrogen chloride in 2-propanol (4 ml) with cooling in an ice bath. The resulting dicyclohexylamine hydrochloride was filtered and washed twice with 2-propanol. The combined filtrate and washings were concentrated under reduced pressure; yield 4.5 g, $[\alpha]_D^{20} -305.1°$ (c 1, methanol).

The (S)(−)-1-(3-benzoylthio-1-oxopropyl)-1,2,3,4-tetrahydro-2-quinolinecarboxylic acid thus obtained (2.1 g) was suspended in a solution of sodium bicarbonate (0.7 g) and water (8 ml) while cooling in an ice bath. This mixture was then freeze dried and the residue was dissolved in methanol (25 ml). This solution was concentrated to 2 ml and then added to 2-propanol (25 ml). The crystalline, (S)(−)-1-(3-benzoylthio-1-oxopropyl)-1,2,3,4-tetrahydro-2-quinolinecarboxylic acid sodium salt, was collected by filtration; yield 1.3 g, m.p. 131°–135°, $[\alpha]_D^{20} -229.3°$ (c 1, methanol).

EXAMPLE 6

(R)(+)-1-(3-Benzoylthio-1-oxopropyl)-1,2,3,4-tetrahydro-2-quinolinecarboxylic Acid A solution of (R)(+)-1,2,3,4-tetrahydro-2-quinolinecarboxylic acid hydrochloride (8.7 g) in pyridine (50 ml) was treated dropwise with 3-benzoylthiopropanoyl chloride (9.4 g) with vigorous stirring. After stirring at room temperature overnight, the mixture was added to ice (700 g) and ether (300 ml). This mixture was acidified with concentrated hydrochloric acid (40 ml) and extracted with ether (700 ml). The ether layer was dried with sodium sulfate and activated charcoal, and then concentrated to dryness to yield a viscous oil (17.5 g). This residue was dissolved in acetonitrile (40 ml) and dicyclohexylamine (9 ml) was added dropwise. The crystalline product was collected by filtration, washed with cold acetonitrile, and ether, and recrystallized from ethanol (60 ml); yield 8.3 g, m.p. 157°–160°, $[\alpha]_D^{20} +158.0°$ (c 1, methanol).

The (R)(+)-1-(3-benzoylthio-1-oxopropyl)-1,2,3,4-tetrahydro-2-quinolinecarboxylic acid dicyclohexylamine salt thus obtained (4.1 g) was suspended in 2-propanol (25 ml) and this mixture was cooled to 5° and treated with a solution of dry hydrogen chloride in 2 propanol unit pH 2. The resulting dicyclohexylamine hydrochloride was filtered and washed twice with 2-propanol. The combined filtrate and washings were concentrated under reduced pressure. The residue was dissolved in ether (30 ml) and filtered and evaporated. This residue in 2-propanol (25 ml) was cooled to 5° and the pH adjusted to 6–7 with 2% sodium hydroxide in ethanol. The product was collected by filtration, washed with 2-propanol, and then ether. The yield of (R)(+)-1-(3-benzoylthio-1-oxopropyl)-1,2,3,4-tetrahydro-2-quinolinecarboxylic acid sodium salt was 2.0 g, m.p. 140°–144°, $[\alpha]_D^{20} +221.3°$ (c 1, methanol).

EXAMPLE 7

(±) 1-(3-Acetylthio-1-oxopropyl)-1,2,3,4-tetrahydro-2-quinolinecarboxylic Acid 3-Acetylthiopropanoic acid (132 g) in toluene (200 ml) was treated with thionyl chloride (300 ml). The resulting solution was warmed on the steam bath for two hours, stirred overnight at room temperature then evaporated to dryness under reduced pressure, and finally distilled, to yield 139 g, b.p. (0.35–0.50 mm) 64°–66° of 3-acetylthiopropanoyl chloride. A solution of (±)-1,2,3,4-tetrahydro-2-quinolinecarboxylic acid hydrochloride (32.05 g) in pyridine (300 ml) was treated dropwise with 3-acetylthiopropanoyl chloride (25 g) with vigorous stirring. After stirring overnight, the reaction mixture was added to ice (600 g), acidified with concentrated hydrochloric acid, and extracted with ether. The combined ether extracts were concentrated under vacuum to a solid product, which was washed with cold ether (50 ml). This product, 1-(3-acetylthio-1-oxopropyl)-1,2,3,4-tetrahydro-2-quinolinecarboxylic acid, was crystallized from ethyl acetate-hexanes; yield 19 g, m.p. 89°–91°.

EXAMPLE 8

(S)(−)-1-(3-Acetylthio-1-oxopropyl)-1,2,3,4-tetrahydro-2-quinolinecarboxylic Acid A solution of (S)(−)-1,2,3,4-tetrahydro-2-quinolinecarboxylic acid hydrochloride (6.4 g) in pyridine (50 ml) was treated dropwise with 3-acetylthiopropanoyl chloride (7.1 g) with vigorous stirring. After stirring at room temperature overnight, the mixture was added to ice (700 g) and then gradually acidified with 20% aqueous hydrochloric acid (130 ml). The resulting mixture was extracted with ether and the extracts washed with water, dried over magnesium sulfate, and concentrated to dryness to yield a viscous oil. The dicyclohexylammonium salt could be prepared by adding dicyclohexylamine to a solution of this crude product in acetone. The resulting (S)(−)-1-(3-acetylthio-1-oxopropyl)-1,2,3,4-tetrahydro-2-quinolinecarboxylic acid dicyclohexylamine salt was recrystallized from 2-propanol (70 ml); yield 6.6 g, m.p. 162°–166°. This salt was converted to the free acid by suspending the salt (6.5 g) in 2-propanol (40 ml) and gradually acidifying the mixture with dry hydrogen chloride in 2-propanol (6 ml) with cooling in an ice bath. The resulting dicyclohexylamine hydrochloride was filtered and washed twice with 2-propanol (20 ml). The combined filtrate and washings were concentrated under reduced pressure. The residue was dissolved in ether (60 ml) and dried over magnesium sulfate and activated charcoal. This solution was evaporated to yield a viscous oil (5 g) which was further purified by column chromatography (silica gel, 5% acetic acid in toluene); yield 2.6 g, m.p. 65°–70°, $[\alpha]_D^{20} -293.1°$ (c 0.5, methanol).

The (S)(−)-1-(3-acetylthio-1-oxopropyl)-1,2,3,4-tetrahydro-2-quinolinecarboxylic acid thus obtained (2.6 g) was dissolved in 2-propanol (35 ml). This solution was cooled to 4° and was treated with a solution of sodium hydroxide (2 g) in ethanol (100 ml). The crystalline, (S)(−)-1-(3-acetylthio-1-oxopropyl)-1,2,3,4-tetrahydro-2-quinolinecarboxylic acid sodium salt, was collected by filtration; yield 1.3 g, m.p. 178°–179°, $[\alpha]_D^{20} -281.2°$ (c 1, methanol).

EXAMPLE 9

(±)-1,2,3,4-Tetrahydro-1-(3-mercapto-1-oxopropyl)-2-quinolinecarboxylic Acid

Procedure A

A mixture of (±)-1-(3-benzoylthio-1-oxopropyl)-1,2,3,4-tetrahydro-2-quinolinecarboxylic acid dicyclohexylamine salt (15 g) and concentrated ammonium hydroxide (280 ml) was heated on the steam bath for 45 minutes with rapid mechanical stirring. After this time, the cooled mixture was filtered through Celite and the filtrate evaporated under reduced pressure to a volume of 25 ml. Water (4 ml) was added and the benzamide was removed by filtration. The filtrate was treated with ether (100 ml) and acidified with 20% aqueous hydrochloric acid (8 ml) while cooling in an ice bath. The dicyclohexylamine hydrochloride was removed by filtration and the filtrate was extracted several times with ether. The combined extracts were dried over sodium sulfate and evaporated to dryness to give a viscous oil (11 g). This product was dissolved in acetone (40 ml) and treated with dicyclohexylamine (5.6 g). The crystalline, (±)-1,2,3,4-tetrahydro-1-(3-mercapto-1-oxopropyl)-2-quinolinecarboxylic acid dicyclohexylamine salt, could be recystallized from 20% acetonitrile in 2-propanol; yield 10 g, m.p. 165°–169°. This salt could be converted to the free acid by suspending the salt (6 g) in 2-propanol (40 ml) and this mixture was cooled to 5° and treated with a solution of dry hydrogen chloride in 2-propanol until pH 2. The resulting dicyclohexylamine hydrochloride was filtered and washed twice with 2-propanol. The combined filtrate and washings were concentrated under reduced pressure. The residue was triturated with carbon tetrachloride to give crystalline product, (±)-1,2,3,4-tetrahydro-1-(3-mercapto-1-oxopropyl)-2-quinolinecarboxylic acid; yield 0.7 g, m.p. 109°–111°.

Procedure B (±)-1-(3-Acetylthio-1-oxopropyl)-1,2,3,4-tetrahydro-2-quinolinecarboxylic acid (28.2 g), concentrated ammonium hydroxide (50 ml), and water (50 ml) were combined and stirred at room temperature under nitrogen for five hours. After this time, concentrated hydrochloric acid was added while cooling with an ice bath until pH 2. The reaction mixture was extracted with ethyl acetate and the combined organic phase was washed with brine, drive over magnesium sulfate, and evaporated to a solid, which was recrystallized from ethyl acetate-hexanes; yield 21 g, m.p. 109°–111°.

A solution of (±)-1,2,3,4-tetrahydro-1-(3-mercapto-1-oxopropyl)-2-quinolinecarboxylic acid thus obtained (1 g) in 2-propanol (16 ml) was treated dropwise with a solution of sodium hydroxide (0.13 g) in ethanol (6.7 ml) at 5°–7° with stirring. After 20 minutes, the resultant white crystalline (±)-1,2,3,4-tetrahydro-1-(3-mercapto-1-oxopropyl)-2-quinolinecarboxylic acid sodium salt was collected by filtration; yield 0.9 g, m.p. 207°–209°.

EXAMPLE 10

(S)(−)-1,2,3,4-Tetrahydro-1-(3-mercapto-1-oxopropyl)-2-quinolinecarboxylic Acid (S)(−)-(3-Benzoylthio-1-oxopropyl)-1,2,3,4-tetrahydro-2-quinolinecarboxylic acid (3 g), concentrated ammonium hydroxide (18 ml), and water (36 ml) were combined and stirred at 40°–45° under nitrogen for three hours. After this time, another portion of concentrated ammonium hydroxide (6 ml) was added and the solution was heated at 40°–45° for an additional three hours under nitrogen. The reaction mixture was then diluted with water (100 ml) and extracted well with ethyl acetate. The aqueous phase was then cooled in an ice bath and the pH adjusted to 2 with concentrated hydrochloric acid. The product was extracted with ether. The extract was dried over sodium sulfate and concentrated under reduced pressure to yield (S)(−)-1,2,3,4-tetrahydro-1-(3-mercapto-1-oxopropyl)-2-quinolinecarboxylic acid; yield 1.6 g, m.p. 130°–132°, $[\alpha]_D^{20}$ −302.3° (c 1, methanol).

EXAMPLE 11

(±)
1,1′-[Dithiobis(1-oxo-3,1-propanediyl)]-bis-1,2,3,4-tetrahydro-2-quinolinecarboxylic Acid (±)-1,2,3,4-Tetrahydro-1-(3-mercapto-1-oxopropyl)-2-quinolinecarboxylic acid (13.27 g) was suspended in water (125 ml) and the pH was adjusted to 6–7 by the addition of 2 N sodium hydroxide. To the resulting clear solution was added 0.5 M iodine in 95% ethanol dropwise while maintaining the pH at 6.5 by the slow addition of 2 N sodium hydroxide. When a yellow color remained for at least five minutes, addition of the iodine solution was termined and the color was discharged with saturated aqueous sodium thiosulfate. The mixture was then acidified with concentrated hydrochloric acid and extracted with ethyl acetate. The combined organic layer was washed with 10% hydrochloric acid and water, dried over magnesium sulfate, and concentrated under reduced pressure to yield 11 g of (±) 1,1′-[dithiobis(1-oxo-3,1-propanediyl)]-bis-1,2,3,4-tetrahydro-2-quinolinecarboxylic acid, m.p. 92°–103° (dec).

EXAMPLE 12

(±)
1-(3-Benzoylthio-2-methyl-1-oxopropyl)-1,2,3,4-tetrahydro-2-quinolinecarboxylic Acid 3-Benzoylthio-2-methylpropanoic acid (11.6 g) in toluene (78 ml) was treated with thionyl chloride (4.6 ml). The resulting solution was warmed to 80° for 2.5 hours and then evaporated to dryness under reduced pressure to yield 3-benzoylthio-2-methylpropanoyl chloride. A solution of (±)-1,2,3,4-tetrahydro-2-quinolinecarboxylic acid hydrochloride (10.7 g) in pyridine (65 ml) was treated dropwise with the crude 3-benzoylthio-2-methylpropanoyl chloride with vigorous stirring. After stirring overnight, the reaction mixture was added to ice (900 g), acidified with 20% hydrochloric acid (130 ml), and extracted with ether (700 ml). The ether layer was dried over sodium sulfate and activated charcoal, and then concentrated to dryness to yield a viscous oil (25 g) which was dissolved in acetonitrile (100 ml) and treated with dicyclohexylamine (13 ml). The crystalline product, (±) 1-(3-benzoyl-2-methyl-1-oxopropyl)-1,2,3,4-tetrahydro-2-quinolinecarboxylic acid dicyclohexylamine salt, was collected by filtration; yield 3.6 g, m.p. 170°–173°.

EXAMPLE 13

(±)
1-(3-Acetylthio-2-methyl-1-oxopropyl)-1,2,3,4-tetrahydro-2-quinolinecarboxylic Acid A solution of (±)-1,2,3,4-tetrahydro-2-quinolinecarboxylic acid hydrochloride (3.2 g) in pyridine (30 ml) was treated dropwise with 3-acetylthio-2-methylpropanoyl chloride (2.7 g) with vigorous stirring. After stirring for three days at room temperature, pyridine hydrochloride was filtered and the filtrate added to ice (300 g). The mixture was acidified with concentrated hydrochloric acid and then extracted with ether. The ether layer was dried over sodium sulfate and silica gel and then concentrated to dryness to yield a viscous oil. Trituration of this oil with carbon tetrachloride gave solid product; yield 5.2 g, m.p. 73°–75°.

The (±) 1-(3-acetylthio-2-methyl-1-oxopropyl)-1,2,3,4-tetrahydro-2-quinolinecarboxylic acid thus obtained was converted to a dicyclohexylamine salt by dissolving the free acid (5.2 g) in acetone (20 ml) and treating with dicyclohexylamine (2.7 ml). The resulting solution was evaporated under reduced pressure to dryness and the viscous oily residue was triturated with petroleum ether. The resulting solid was recrystallized from cyclohexane; yield 4.5 g, m.p. 133°–135°.

EXAMPLE 14

(±)
1-(3-Acetylthio-2-acetylthiomethyl-1-oxopropyl)-
1,2,3,4-tetrahydro-2-quinolinecarboxylic Acid A solution of (±)-1,2,3,4-tetrahydro-2-quinolinecarboxylic acid hydrochloride (14.52 g) in pyridine (150 ml) was treated dropwise with 3-acetylthio-2-(acetylthiomethyl)propanoyl chloride with vigorous stirring. After stirring overnight at room temperature, the mixture was added to ice (300 g) and the pH was adjusted to 2.5 with concentrated hydrochloric acid. The mixture was extracted with ether and the ether extract dried over sodium sulfate and evaporated to a syrup. This (±) 1-(3-acetylthio-2-acetylthiomethyl-1-oxopropyl)-1,2,3,4-tetrahydro-2-quinolinecarboxylic acid was further purified by column chromatography (silica gel, toluene:ethyl acetate:acetic acid, 6.5:3:0.5); yield 2.5 g, m.p. 149°–151°.

EXAMPLE 15

(−)-1-[(2R) and
(2S)-3-Acetylthio-2-methyl-1-oxopropyl]-(2S)-1,2,3,4-tetrahydro-2-quinolinecarboxylic Acid A solution of (S)(−)-1,2,3,4-tetrahydro-2-quinolinecarboxylic acid hydrochloride (6.4 g) in pyridine (60 ml) was treated dropwise with 3-acetylthio-2-methylpropanoyl chloride (5.4 g) with vigorous stirring. After stirring overnight at room temperature, the mixture was added to ice (500 g) and the pH was adjusted to 2 with 20% hydrochloric acid (110 ml). The mixture was extracted with ether and the ether extracts dried over sodium sulfate, activated charcoal, and silica gel. The solvent was removed under reduced pressure to yield a viscous oil (13 g) which showed two main spots on thin layer chromatography, Rf 0.25 and 0.32 (silica gel; chloroform:methanol:acetic acid, 64:1:1). These two diastereomers, (−)-1-[(2R)-3-acetylthio-2-methyl-1-oxopropyl]-(2S)-1,2,3,4-tetrahydro-2-quinolinecarboxylic acid and (−)-1-[(2S)-3-acetylthio-2-methyl-1-oxopropyl]-(2S)-1,2,3,4-tetrahydro-2-quinolinecarboxylic acid, were separated by column chromatography (silica gel, chloroform:methanol:acetic acid, 64:1:1), yield 3.5 g of the faster moving diastereomer, m.p. 124°–127°, $[\alpha]_D^{20} - 176.4°$ (c 0.5, methanol); yield 3.5 g of the slower moving diastereomer, m.p. 84°–92°, $[\alpha]_D^{20} - 360.9°$ (c 1, methanol).

EXAMPLE 16

(±)-1,2,3,4-Tetrahydro-1-(3-mercapto-2-methyl-1-oxopropyl)-2-quinolinecarboxylic Acid (±) 1-(3-Acetylthio-2-methyl-1-oxopropyl)-1,2,3,4-tetrahydro-2-quinolinecarboxylic acid (26 g), concentrated ammonium hydroxide (55 ml), and water (110 ml) were combined and stirred at room temperature under nitrogen for six hours. After this time, concentrated hydrochloric acid was added while cooling with an ice bath until pH 2. The reaction mixture was extracted with ether (150 ml) and the extract dried over sodium sulfate, and evaporated to an oil. This residue, (±)-1,2,3,4-tetrahydro-1-(3-mercapto-2-methyl-1-oxopropyl)-2-quinolinecarboxylic acid, was crystallized from toluene; yield 4.5 g, m.p. 98°–101°.

EXAMPLE 17

(±)
1-(2-Benzoylthio-1-oxoethyl)-1,2,3,4-tetrahydro-2-quinolinecarboxylic Acid (±)-1,2,3,4-Tetrahydro-2-quinolinecarboxylic acid hydrochloride (26 g) was dissolved in a cold solution of sodium hydroxide (9.6 g) and water (125 ml). The solution was cooled with an ice bath and under vigorous stirring, a solution of sodium hydroxide (4.8 g) and water (60 ml), and chloroacetyl chloride (9.9 ml) were added dropwise. The mixture was stirred for three hours at room temperature and then potassium thiobenzoate (21 g) in water (120 ml) was added. This mixture was stirred at room temperature for eighteen hours, cooled in an ice bath to 0°, and then acidified with concentrated hydrochloric acid. The product was extracted with chloroform and the extract dried over magnesium sulfate and concentrated to yield (±)-1-(2-benzoylthio-1-oxoethyl)-1,2,3,4-tetrahydro-2-quinolinecarboxylic acid; yield 29 g, m.p. 164°–168°.

EXAMPLE 18

(±)-1,2,3,4-Tetrahydro-1-(2-mercapto-1-oxoethyl)-2-quinolinecarboxylic Acid (±) 1-(2-Benzoyl-1-oxoethyl)-1,2,3,4-tetrahydro-2-quinolinecarboxylic acid (29 g), concentrated ammonium hydroxide (53 ml) and water (106 ml) were combined and stirred at room temperature under nitrogen for three hours. After this time, the benzamide was filtered and water (150 ml) was added to the filtrate. This solution was extracted with ethyl acetate and then the aqueous phase was acidified with concentrated hydrochloric acid. The product was then extracted with chloroform and after drying over sodium sulfate and evaporation, (±)-1,2,3,4-tetrahydro-1-(2-mercapto-1-oxoethyl)-2-quinolinecarboxylic acid was obtained; yield 9.0 g, m.p. 85°–86°.

The free acid was converted to a dicyclohexylamine salt by dissolving the free acid (10 g) in acetone (150 ml) and then adding dicyclohexylamine until pH 8 was reached. The resulting (±)-1,2,3,4-tetrahydro-1-(2-mercapto-1-oxoethyl)-2-quinolinecarboxylic acid dicyclohexylamine salt was collected by filtration; yield 16 g, m.p. 154°–156°.

The free acid was converted to a sodium salt by suspending the free acid (5 g) in 2-propanol (80 ml) and cooling to 5°. The resulting solution was adjusted to pH 6-7 with 2 N sodium hydroxide (40 ml) in ethanol. The (±)-1,2,3,4-tetrahydro-1-(2-mercapto-1-oxoethyl-2-quinolinecarboxylic acid sodium salt was collected by filtration; yield 5 g, m.p. 185°–188°.

EXAMPLE 19

(±)
1,1'-[Dithiobis(1-oxo-2,1-ethanediyl)]-bis-1,2,3,4-tetrahydro-2-quinolinecarboxylic Acid (±)-1,2,3,4-Tetrahydro-1-(2-mercapto-1-oxoethyl)-2-quinolinecarboxylic acid (3 g) was suspended in water (40 ml) and the pH was adjusted to 6.5 with 2 N sodium hydroxide. A saturated solution of iodine in ethanol was then added dropwise while maintaining the pH at 6.5 by the slow addition of 2 N sodium hydroxide. When a yellow color remained for at least five minutes, addition of the iodine solution was terminated and the yellow color was discharged with saturated aqueous sodium thiosulfate. The mixture was then acidified with concentrated hydrochloric acid and extracted with ethyl acetate. The combined extracts were washed with 10% hydrochloric acid and water, dried over magnesium sulfate, and concentrated under reduced pressure. The (±) 1,1'-[dithiobis(1-oxo-2,1-ethanediyl)]-bis-1,2,3,4-tetrahydro-2-quinolinecarboxylic acid was recrystallized from ethyl acetate; yield 0.7 g, m.p. 172°–174°.

EXAMPLE 20

(±)-1-(2-Benzoylthio-1-oxopropyl)-1,2,3,4-tetrahydro-2-quinolinecarboxylic Acid (±)-1,2,3,4-Tetrahydro-2-quinolinecarboxylic acid hydrochloride (43 g) in pyridine (300 ml) was treated dropwise with 2-benzoylthiopropanoyl chloride (46 g) with vigorous stirring. After stirring at room temperature overnight, the mixture was poured onto ice (300 g) and acidified with concentrated hydrochloric acid. The product was extracted with ether and the ether extracts combined, dried over sodium sulfate, and concentrated to dryness in vacuo. The residue, (±)-1-(2-benzoylthio-1-oxopropyl)-1,2,3,4-tetrahydro-2-quinolinecarboxylic acid, was crystallized from acetonitrile (100 ml); yield 7 g, m.p. 157°–159°.

EXAMPLE 21

(±)-1-(2-Mercapto-1-oxopropyl)-1,2,3,4-tetrahydro-2-quinolinecarboxylic Acid (±)-1-(2-Benzoylthio-1-oxopropyl)-1,2,3,4-tetrahydro-2-quinolinecarboxylic acid (4.5 g), concentrated ammonium hydroxide (8 ml) and water (16 ml) were combined and stirred at room temperature under nitrogen for three hours. The benzamide was filtered and the filtrate diluted with water (25 ml). The reaction mixture was then extracted with ethyl acetate and acidified with concentrated hydrochloric acid. The product was extracted with chloroform and the chloroform extracts dried over sodium sulfate and activated charcoal, and concentrated in vacuo. The residue, (±)-1-(2-mercapto-1-oxopropyl)-1,2,3,4-tetrahydro-2-quinolinecarboxylic acid, was triturated with carbon tetrachloride (20 ml); yield 3.2 g, m.p. 141°–143°.

EXAMPLE 22

(±)-1,2,3,4-Tetrahydro-6-methoxy-2-quinolinecarboxylic Acid Hydrochloride

By substituting 6-methoxy-2-quinolinecarboxylic acid (45 g) for the 2-quinolinecarboxylic acid in the procedure of Example 1, (±)-1,2,3,4-tetrahydro-6-methoxy-2-quinolinecarboxylic acid hydrochloride was obtained; yield 32.7 g, m.p. 200° (dec).

EXAMPLE 23

(±)-1-(3-Benzoylthio-1-oxopropyl)-1,2,3,4-tetrahydro-6-methoxy-2-quinolinecarboxylic Acid A stirred solution of (±)-1,2,3,4-tetrahydro-6-methoxy-2-quinolinecarboxylic acid hydrochloride (3 g) and 1 N sodium hydroxide (25 ml) was cooled in an ice bath. 3-Chloropropionyl chloride (1.7 ml) and 2 N sodium hydroxide (6 ml) were added dropwise over five minutes.

When addition was complete, the pH was adjusted to 7.5–8.5 with 2 N sodium hydroxide and stirring was continued at room temperature for four hours. The solution was then cooled in an ice bath and 6 N hydrochloric acid was added until pH 2. The resulting mixture was extracted with chloroform and the extracts were combined and washed with water (100 ml), brine (100 ml), 0.5 N hydrochloric acid (200 ml), water (100 ml), and brine (100 ml). After drying over magnesium sulfate and activated charcoal, the solution was concentrated in vacuo to a viscous oil. This oily residue was dissolved in N,N-dimethylformamide (40 ml) and then potassium thiobenzoate (2 g) was added and the mixture stirred at room temperature for twenty hours. After this time, the solution was poured into ice (300 g) and then extracted with ethyl acetate. The extracts were combined and washed well with water, brine, and 0.5 N hydrochloric acid, dried over magnesium sulfate, and concentrated in vacuo to the oily residue, (±) 1-(3-benzoylthio-1-oxopropyl)-1,2,3,4-tetrahydro-6-methoxy-2-quinolinecarboxylic acid. The dicyclohexylamine salt was prepared by the addition of dicyclohexylamine to a solution of the free acid in acetonitrile; yield 1.6 g, m.p. 158°–160°.

EXAMPLE 24

(±)-1,2,3,4-Tetrahydro-1-(3-mercapto-1-oxopropyl)-6-methoxy-2-quinolinecarboxylic Acid By substituting (±) 1-(3-benzoylthio-1-oxopropyl)-1,2,3,4-tetrahydro-6-methoxy-2-quinolinecarboxylic acid for the (±) 1-(2-benzoylthio-1-oxopropyl)-1,2,3,4-tetrahydro-2-quinolinecarboxylic acid in the procedure of Example 21, (±)-1,2,3,4-tetrahydro-1-(3-mercapto-1-oxopropyl)-6-methoxy-2-quinolinecarboxylic acid was obtained as an oily residue. The dicyclohexylamine salt was prepared by the addition of dicyclohexylamine to a solution of the free acid in ether. The (±)-1,2,3,4-tetrahydro-1-(3-mercapto-1-oxopropyl)-6-methoxy-2-quinolinecarboxylic acid dicyclohexylamine salt thus obtained was recrystallized from acetonitrile; yield 0.9 g, m.p. 195°–197°.

EXAMPLE 25

(±)-1,2,3,4-Tetrahydro-6,7-dimethoxy-2-quinolinecarboxylic Acid Hydrochloride

By substituting 6,7-dimethoxy-2-quinolinecarboxylic acid for the 2-quinolinecarboxylic acid in the procedure of Example 1, (±)-1,2,3,4-tetrahydro-6,7-dimethoxy-2-quinolinecarboxylic acid hydrochloride was obtained.

EXAMPLE 26

(±)-1-(3-Acetylthio-1-oxopropyl)-1,2,3,4-tetrahydro-6,7-dimethoxy-2-quinolinecarboxylic Acid By substituting (±)-1,2,3,4-tetrahydro-6,7-dimethoxy-2-quinolinecarboxylic acid hydrochloride (13.5 g) for the (±)-1,2,3,4-tetrahydro-2-quinolinecarboxylic acid hydrochloride in the procedure of Example 7, (±)-1-(3-acetylthio-1-oxopropyl)-1,2,3,4-tetrahydro-6,7-dimethoxy-2-quinolinecarboxylic acid was obtained. The product was further purified by column chromatography (silica gel; ethyl acetate; acetone; acetic acid: 9:0.5:0.5); yield 2.7 g, m.p. 104°–107°.

EXAMPLE 27

6-Methyl-2-quinolinecarboxylic Acid

6-Methylquinoline (100 g) was dissolved in methylene chloride (840 ml) and a solution of potassium cyanide (136 g) in water (340 ml) was added. The resulting mixture was stirred and benzoyl chloride (162 ml) was added dropwise over six hours. Stirring was then continued overnight at room temperature. After this time, the mixture was filtered through Celite, and the aqueous layer extracted with methylene chloride. The combined organic layer and extracts were washed with water, 1 N hydrochloric acid, water, 1 N sodium hydroxide, and water, dried over magnesium sulfate, and concentrated in vacuo to a solid residue. This product was recrystallized from ethanol; yield 155.2 g, m.p. 145°–147°.

The resulting (±) 1-benzoyl-2-cyano-1,2-dihydro-6-methylquinoline thus obtained (155.2 g) was added to acetic acid (170 ml) and 48% hydrobromic acid (170 ml) and this mixture was stirred and refluxed for 0.5 hours. After cooling to room temperature, the solid was collected by filtration and then stirred in water (1000 ml) at 80°–90° while concentrated ammonium hydroxide was added until a pH of 8–9 was obtained. After cooling to 50°, acetic acid was added until a pH of 4–5 was reached. The 6-methyl-2-quinolinecarboxylic acid was collected by filtration and then recrystallized from acetic acid; yield 87 g, m.p. 208° (dec).

EXAMPLE 28

(±)-1,2,3,4-Tetrahydro-6-methyl-2-quinolinecarboxylic Acid Hydrochloride

By substituting 6-methyl-2-quinolinecarboxylic acid (45 g) for the 2-quinolinecarboxylic acid in the procedure of Example 1, (±)-1,2,3,4-tetrahydro-6-methyl-2-quinolinecarboxylic acid hydrochloride was obtained; yield 46 g.

EXAMPLE 29

(±) 1-(3-Acetylthio-1-oxopropyl)-1,2,3,4-tetrahydro-6-methyl-2-quinolinecarboxylic Acid By substituting (±)-1,2,3,4-tetrahydro-6-methyl-2-quinolinecarboxylic acid hydrochloride (30 g) for the (S)(−)-1,2,3,4-tetrahydro-2-quinolinecarboxylic acid hydrochloride in the procedure of Example 8, (±) 1-(3-acetylthio-1-oxopropyl)-1,2,3,4-tetrahydro-6-methyl-2-quinolinecarboxylic acid dicyclohexylamine salt; yield 33.7 g, and (±) 1-(3-acetylthio-1-oxopropyl)-1,2,3,4-tetrahydro-6-methyl-2-quinolinecarboxylic acid; yield 3.8 g, m.p. 118°–120° were obtained.

EXAMPLE 30

7-Methyl-2-quinolinecarboxylic Acid

By substituting 7-methylquinoline (100 g) for the 6-methylquinoline in the procedure of Example 28, 1-benzoyl-2-cyano-1,2-dihydro-7-methylquinoline; yield 138 g, m.p. 160°–162°, and 7-methyl-2-quinolinecarboxylic acid; yield 61.5 g, were obtained.

EXAMPLE 31

(±)-1,2,3,4-Tetrahydro-7-methyl-2-quinolinecarboxylic Acid Hydrochloride

By substituting 7-methyl-2-quinolinecarboxylic acid (41 g) for 2-quinolinecarboxylic acid in the procedure of Example 1, (±)-1,2,3,4-tetrahydro-7-methyl-2-quinolinecarboxylic acid hydrochloride; yield 38.1 g, was obtained.

EXAMPLE 32

(±) 1-(3-Acetylthio-1-oxopropyl)-1,2,3,4-tetrahydro-7-methyl-2-quinolinecarboxylic Acid By substituting (±)-1,2,3,4-tetrahydro-7-methyl-2-quinolinecarboxylic acid hydrochloride (30 g) for the (S)(−)-1,2,3,4-tetrahydro-2-quinolinecarboxylic acid hydrochloride in the procedure of Example 8, (±) 1-(3-acetylthio-1-oxopropyl)-1,2,3,4-tetrahydro-7-methyl-2-quinolinecarboxylic acid dicyclohexylamine salt; yield 41.9 g, m.p. 153°–157°, and (±) 1-(3-acetylthio-1-oxopropyl)-1,2,3,4-tetrahydro-7-methyl-2-quinolinecarboxylic acid; yield 8.5 g, m.p. 119°–122° were obtained.

EXAMPLE 33

6-Chloro-2-quinolinecarboxylic Acid

By substituting 6-chloroquinoline (75 g) for the 6-methylquinoline in the procedure of Example 28, 1-benzoyl-2-cyano-1,2-dihydro-6-chloroquinoline; yield 98 g, m.p. 140°–143°, and 6-chloro-2-quinolinecarboxylic acid; yield 51.5 g, m.p. 231°–232° (dec) were obtained.

EXAMPLE 34

(±)-6-Chloro-1,2,3,4-tetrahydro-2-quinolinecarboxylic Acid Hydrochloride

By substituting 6-chloro-2-quinolinecarboxylic acid for 2-quinolinecarboxylic acid in the procedure of Example 1, (±)-6-chloro-1,2,3,4-tetrahydro-2-quinolinecarboxylic acid hydrochloride; yield 31.7 g, was obtained.

EXAMPLE 35

(±) 1-(3-Acetylthio-1-oxopropyl)-6-chloro-1,2,3,4-tetrahydro-2-quinolinecarboxylic Acid By substituting (±)-6-chloro-1,2,3,4-tetrahydro-2-quinolinecarboxylic acid hydrochloride (20 g) for the (S)(−)-1,2,3,4-tetrahydro-2-quinolinecarboxylic acid hydrochloride in the procedure of Example 8, (±) 1-(3-acetylthio-1-oxopropyl)-6-chloro-1,2,3,4-tetrahydro-2-quinolinecarboxylic acid dicyclohexylamine salt; yield 20.5 g, and (±) 1-(3-acetylthio-1-oxopropyl)-6-chloro-1,2,3,4-tetrahydro-2-quinolinecarboxylic acid; yield 1.6 g, m.p. 134°–136° were obtained.

EXAMPLE 36

6-Hydroxy-2-quinolinecarboxylic Acid

6-Methoxy-2-quinolinecarboxylic acid (80.6 g) was refluxed in 48% hydrobromic acid (450 ml) for twenty-four hours. After cooling to room temperature, the solid was collected by filtration and then dissolved in water (1300 ml) at 90° and the pH of this solution was adjusted to 8–9 with concentrated ammonium hydroxide. After cooling to room temperature, the pH of this solution was adjusted to 4–5 with acetic acid. The resulting 6-hydroxy-2-quinolinecarboxylic acid was collected by filtration and washed with water (400 ml); yield 70 g, m.p. 260°–261° (dec).

EXAMPLE 37

(±)-1,2,3,4-Tetrahydro-6-hydroxy-2-quinolinecarboxylic Acid Hydrochloride

By substituting 6-hydroxy-2-quinolinecarboxylic acid (28 g) for 2-quinolinecarboxylic acid in the procedure of Example 1, (±)-1,2,3,4-tetrahydro-6-hydroxy-2-quinolinecarboxylic acid hydrochloride; yield 21.5 g, m.p. 177°–179° (dec), was obtained.

EXAMPLE 38

(±)-1-(3-Acetylthio-1-oxopropyl)-1,2,3,4-tetrahydro-6-hydroxy-2-quinolinecarboxylic Acid By substituting (±)-1,2,3,4-tetrahydro-6-hydroxy-2-quinolinecarboxylic acid hydrochloride (21.5 g) for (±)-1,2,3,4-tetrahydro-2-quinolinecarboxylic acid hydrochloride in the procedure of Example 7, (±)-1-(3-acetylthio-1-oxopropyl)-1,2,3,4-tetrahydro-6-hydroxy-2-quinolinecarboxylic acid; yield 2.9 g, m.p. 150°–152° was obtained.

What is claimed is:

1. The dicyclohexylamine salt of 1-[(3-benzoylthio)-1-oxopropyl]-1,2,3,4-tetrahydroquinoline-2-carboxylic acid.

2. The sodium salt of 1-[(3-benzoylthio)-1-oxopropyl]-1,2,3,4-tetrahydroquinoline-2-carboxylic acid.

3. The dicyclohexylamine salt of 1,2,3,4-tetrahydro-1-[(3-mercapto)-1-oxopropyl]-quinoline-2-carboxylic acid.

4. A compound of the formula:

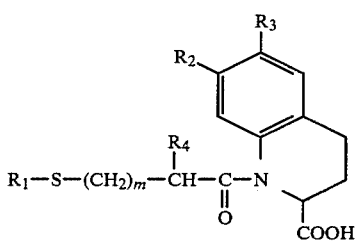

wherein $R_1$ is benzoyl, acetyl, hydrogen or

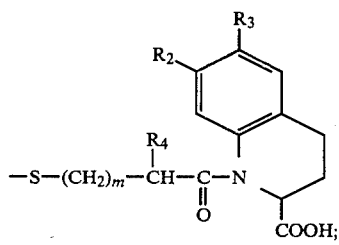

$R_2$ is hydrogen, methoxy or methyl; $R_3$ is hydrogen, methoxy, methyl, chloro or hydroxy; $R_4$ is hydrogen, methyl or acetylthiomethyl; m is 0 or 1 and the sodium and dicyclohexylamine salts thereof.

5. The compound (±)-1-(3-benzoylthio-1-oxopropyl)-1,2,3,4-tetrahydro-2-quinolinecarboxylic acid.

6. The dicyclohexylamine salt of (S)(−)-1-(3-benzoylthio-1-oxopropyl)-1,2,3,4-tetrahydro-2-quinolinecarboxylic acid.

7. The compound (S)(−)-1-(3-benzoylthio-1-oxopropyl)-1,2,3,4-tetrahydro-2-quinolinecarboxylic acid.

8. The sodium salt of (S)(−)-1-(3-benzoylthio-1-oxopropyl)-1,2,3,4-tetrahydro-2-quinolinecarboxylic acid.

9. The dicyclohexylamine salt of (R)(+)-1-(3-benzoylthio-1-oxopropyl)-1,2,3,4-tetrahydro-2-quinolinecarboxylic acid.

10. The sodium salt of (R)(+)-1-(3-benzoylthio-1-oxopropyl)-1,2,3,4-tetrahydro-2-quinolinecarboxylic acid.

11. The compound (±)-1-(3-acetylthio-1-oxopropyl)-1,2,3,4-tetrahydro-2-quinolinecarboxylic acid.

12. The sodium salt of (S)(−)-1-(3-acetylthio-1-oxopropyl)-1,2,3,4-tetrahydro-2-quinolinecarboxylic acid.

13. The compound (S)(−)-1-(3-acetylthio-1-oxopropyl)-1,2,3,4-tetrahydro-2-quinolinecarboxylic acid.

14. The compound (±)-1-(3-mercapto-1-oxopropyl)-1,2,3,4-tetrahydro-2-quinolinecarboxylic acid.

15. The sodium salt of (±)-1-(3-mercapto-1-oxopropyl)-1,2,3,4-tetrahydro-2-quinolinecarboxylic acid.

16. The compound (S)(−)-1-(3-mercapto-1-(oxopropyl)-1,2,3,4-tetrahydro-2-quinolinecarboxylic acid.

17. The compound (±) 1,1'-[dithiobis(1-oxo-3,1-propanediyl]-bis-1,2,3,4-tetrahydro-2-quinolinecarboxylic acid.

18. The compound (±)-1-(3-benzoylthio-2-methyl-1-oxopropyl)-1,2,3,4-tetrahydro-2-quinolinecarboxylic acid.

19. The dicyclohexylamine salt of (±)-1-(3-acetylthio-2-methyl-1-oxopropyl)-1,2,3,4-tetrahydro-2-quinolinecarboxylic acid.

20. The compound (±)-1-(3-acetylthio-2-methyl-1-oxopropyl)-1,2,3,4-tetrahydro-2-quinolinecarboxylic acid.

21. The compound (±)-1-(3-acetylthio-2-acetylthiomethyl-1-oxopropyl)-1,2,3,4-tetrahydro-2-quinolinecarboxylic acid.

22. The compound (−)-1-[(2R)-3-acetylthio-2-methyl-1-oxopropyl]-(2S)-1,2,3,4-tetrahydro-2-quinolinecarboxylic acid.

23. The compound (−)-1-[(2S)-3-acetylthio-2-methyl-1-oxopropyl]-(2S)-1,2,3,4-tetrahydro-2-quinolinecarboxylic acid.

24. The compound (±)-1-(3-mercapto-2-methyl-1-oxopropyl)-1,2,3,4-tetrahydro-2-quinolinecarboxylic acid.

25. The compound (±)-1-(2-benzoylthio-1-oxoethyl)-1,2,3,4-tetrahydro-2-quinolinecarboxylic acid.

26. The dicyclohexylamine salt of (±)-1-(2-mercapto-1-oxoethyl)-1,2,3,4-tetrahydro-2-quinolinecarboxylic acid.

27. The sodium salt of (±)-1-(2-mercapto-1-oxoethyl)-1,2,3,4-tetrahydro-2-quinolinecarboxylic acid.

28. The compound (±)-1-(2-mercapto-1-oxoethyl)-1,2,3,4-tetrahydro-2-quinolinecarboxylic acid.

29. The compound (±)-1,1'-[dithiobis(1-oxo-2,1-ethanediyl)]-bis-1,2,3,4-tetrahydro-2-quinolinecarboxylic acid.

30. The compound (±)-1-(2-benzoylthio-1-oxopropyl)-1,2,3,4-tetrahydro-2-quinolinecarboxylic acid.

31. The compound (±)-1-(2-mercapto-1-oxopropyl)-1,2,3,4-tetrahydro-2-quinolinecarboxylic acid.

32. The compound (±)-1-(3-benzoylthio-1-oxopropyl)-1,2,3,4-tetrahydro-6-methoxy-2-quinolinecarboxylic acid.

33. The dicyclohexylamine salt of (±)-1-(3-mercapto-1-oxopropyl)-1,2,3,4-tetrahydro-6-methoxy-2-quinolinecarboxylic acid.

34. The compound (±)-1-(3-acetylthio-1-oxopropyl)-1,2,3,4-tetrahydro-6,7-dimethoxy-2-quinolinecarboxylic acid.

35. The compound (±)-1-(3-acetylthio-1-oxopropyl)-1,2,3,4-tetrahydro-6-methyl-2-quinolinecarboxylic acid.

36. The dicyclohexylamine salt of (±)-1-(3-acetylthio-1-oxopropyl)-1,2,3,4-tetrahydro-7-methyl-2-quinolinecarboxylic acid.

37. The compound (±)-1-(3-acetylthio-1-oxopropyl)-1,2,3,4-tetrahydro-7-methyl-2-quinolinecarboxylic acid.

38. The compound (±)-1-(3-acetylthio-1-oxopropyl)-6-chloro-1,2,3,4-tetrahydro-2-quinolinecarboxylic acid.

39. The compound (±)-1-(3-acetylthio-1-oxopropyl)-1,2,3,4-tetrahydro-6-hydroxy-2-quinolinecarboxylic acid.

* * * * *